(12) United States Patent
Osipov

(10) Patent No.: US 6,966,885 B2
(45) Date of Patent: Nov. 22, 2005

(54) HYDROTHERAPY PROCESS AND APPARATUS

(75) Inventor: Andre Osipov, 1841 Evergreen St., San Mateo, CA (US) 94401

(73) Assignee: Andre Osipov, San Mateo, CA (US)

( * ) Notice: Subject to any disclaimer, the term of this patent is extended or adjusted under 35 U.S.C. 154(b) by 0 days.

(21) Appl. No.: 10/934,607

(22) Filed: Sep. 2, 2004

(65) Prior Publication Data

US 2005/0054964 A1 Mar. 10, 2005

Related U.S. Application Data

(60) Provisional application No. 60/501,540, filed on Sep. 8, 2003.

(51) Int. Cl.$^7$ ................................ A61F 5/00
(52) U.S. Cl. ................ 602/36; 602/32; 482/111; 482/55
(58) Field of Search ............... 602/32–36; 4/496, 4/494, 487, 506, 560–566; 5/63, 90; 482/11, 482/111; 441/136; 601/158; 128/870

(56) References Cited

U.S. PATENT DOCUMENTS

| | | |
|---|---|---|
| 1,915,371 A | 6/1933 | Lowman |
| 3,981,484 A | 9/1976 | James |
| 4,149,712 A | 4/1979 | Murphy |
| 4,183,106 A | 1/1980 | Grimes et al. |
| 4,283,803 A | 8/1981 | Krumbeck |
| 4,551,108 A | 11/1985 | Bass |
| 4,588,155 A | 5/1986 | James |
| 4,700,696 A | 10/1987 | Schoffstall |
| 4,712,788 A | 12/1987 | Gaudreau, Jr. |
| 4,722,329 A | 2/1988 | Kalvåg |
| 4,875,673 A | 10/1989 | Erickson |
| 4,885,810 A * | 12/1989 | Unger et al. ............ 4/496 |
| 4,941,216 A * | 7/1990 | Boublil ............ 4/496 |
| 5,050,863 A | 9/1991 | Yacoboski |
| 5,078,126 A | 1/1992 | Perry |
| 5,218,727 A | 6/1993 | Krumbeck |
| 5,367,721 A | 11/1994 | Boyles |
| 5,465,433 A | 11/1995 | Nolan |
| 5,715,545 A | 2/1998 | Forwick |
| 5,752,899 A | 5/1998 | Ballard |
| 5,885,194 A | 3/1999 | Wasserman et al. |
| 6,042,602 A * | 3/2000 | Wells ............ 606/241 |
| 6,273,867 B1 | 8/2001 | Glazer |
| 6,796,953 B2 * | 9/2004 | Aduana et al. ............ 602/32 |
| 6,860,272 B2 * | 3/2005 | Carter et al. ............ 128/870 |

* cited by examiner

*Primary Examiner*—Henry Bennett
*Assistant Examiner*—Shumaya B. Ali
(74) *Attorney, Agent, or Firm*—Townsend and Townsend and Crew LLP

(57) ABSTRACT

This invention relates to hydrotherapy where a patient is placed in traction while immersed in a heated hydrotherapy pool. More specifically, a process and apparatus for hydrotherapy traction is disclosed in which the patient is placed in a horizontal supine position, and gradually moved to and from a position of immersed hydrotherapy traction in the heated hydrotherapy pool.

8 Claims, 4 Drawing Sheets

HYDROTHERAPY PROCESS AND APPARATUS

CROSS-REFERENCES TO RELATED APPLICATIONS

This application claims the benefit under 35 USC 119(e) of provisional patent application 60/501,540 filed Sep. 8, 2003 entitled "Hydrotherapy Process And Apparatus."

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK

NOT APPLICABLE

This invention relates to traction of patients in water, otherwise know as hydrotherapy traction. More specifically, and apparatus and process for placing a patient into and out of a pool in which traction occurs is disclosed.

BACKGROUND OF THE INVENTION

Traction in a heated pool can be highly beneficial. In such traction, the patient is typically suspended from the upper body, such as suspension by the shoulders in a harness. At the same time, weights are applied to the waist of the patient. The patient, fitted with the harness and weights, typically walks into or is moved into the vertical traction position in a heated hydrotherapy pool.

Unfortunately, this treatment has an extraordinary drawback. Upon leaving traction under hydrotherapy, extraordinary pain is a common phenomena. Specifically, the patient experiences an immediate reversal of the traction. The tensile forces on the patient's spine are immediately reversed as the patient walks or climbs from the hydrotherapy pool. It is common for such patients to experience such extraordinary pain that they fall to their hands and knees refusing to move until time passes and the pain begins to subside. to be solved. As the discovery of the problem to be solved can constitute invention, insofar as mention of this problem has not been made elsewhere, I claim invention.

Perry U.S. Pat. No. 5,078,126 entitled Flotation Controlled Spinal Decompression is an example of hydrotherapy administered in the vertical disposition. The patient is suspended in a heated pool. Suspension occurs either by the head or, alternatively, by a flotation jacket exerting a buoyant upward force at the shoulders. The waist of the patient is weighted. Between the shoulders and the waist the patient is subject to tension during traction. At the same time the patient is typically immersed in heated water so that the required therapy occurs.

BRIEF SUMMARY OF THE INVENTION

A patient is placed in a supine position on a horizontal immersible stretcher. A harness secured to the stretcher is placed to support the patient, typically under the arms. The patient's lower body, typically at the waist has weights attached sufficient to render the desired hydrotherapy traction. Thereafter, the immersible stretcher is moved from the horizontal position to the vertical position with the patient gradually being immersed in a heated hydrotherapy pool. Movement preferably occurs over an arcuate surface sloping from the horizontal to the vertical adjacent the pool. Once in the hydrotherapy pool, the patient is given sufficient dwell time—usually on the order of 15 to 30 minutes—to administer the desired hydrotherapy traction. After this period of time, the patient and immersible stretcher are gradually moved from the vertical position to the supine horizontal position. The harness and weights are removed. A support belt is placed around the patient at the waist. After a sufficient rest period, the patient gradually arises. The resulting processes take place without or with vastly reduced pain for the patient.

An advantage of this hydrotherapy traction procedure is that an immediate reversal of the traction forces on the patient's spine does not occur. In the normal case, where the patient leaves the hydrotherapy pool by walking or climbing, the spine goes from traction to gravitational compression immediately upon exit from the pool. It is believed that this immediate reversal of stresses on the spine is the cause of the excruciating pain common to the prior art treatments. By placing the patient in a supine position immediately after traction, the traction force gradually relaxes to a neutral force on the spine. By letting the patient rest in the horizontal position, the traction force naturally progresses to a neutral force on the spine. Thereafter, and before the spine undergoes gravitational compression, a support belt is placed about the abdomen of the patient. When the patient does arise, such movement is relatively painless.

BRIEF DESCRIPTION OF THE DRAWINGS

FIGS. 1A to 1D are a cartoon series of the process and apparatus of this invention in which:

FIG. 1A illustrates the patient in the supine or horizontal position on the immersible stretcher at the horizontal portion of the sloping surface with the harness attached at the shoulders and weights placed around the waist ready for immersion to the hydrotherapy pool;

FIG. 1B illustrates the patient being moved from the supine horizontal position on the immersible stretcher to an angular partially immersed position within the hydrotherapy pool;

FIG. 1C illustrates the patient in the vertical hydrotherapy traction position within the pool clear of the sloping surface; and, FIG. 1D illustrates the patient in the supine horizontal position on the immersible stretcher after the weights have been removed, and the harness released, with a support belt placed around the abdomen for providing support after the therapy.

DETAILED DESCRIPTION OF THE INVENTION

Figure 1A:
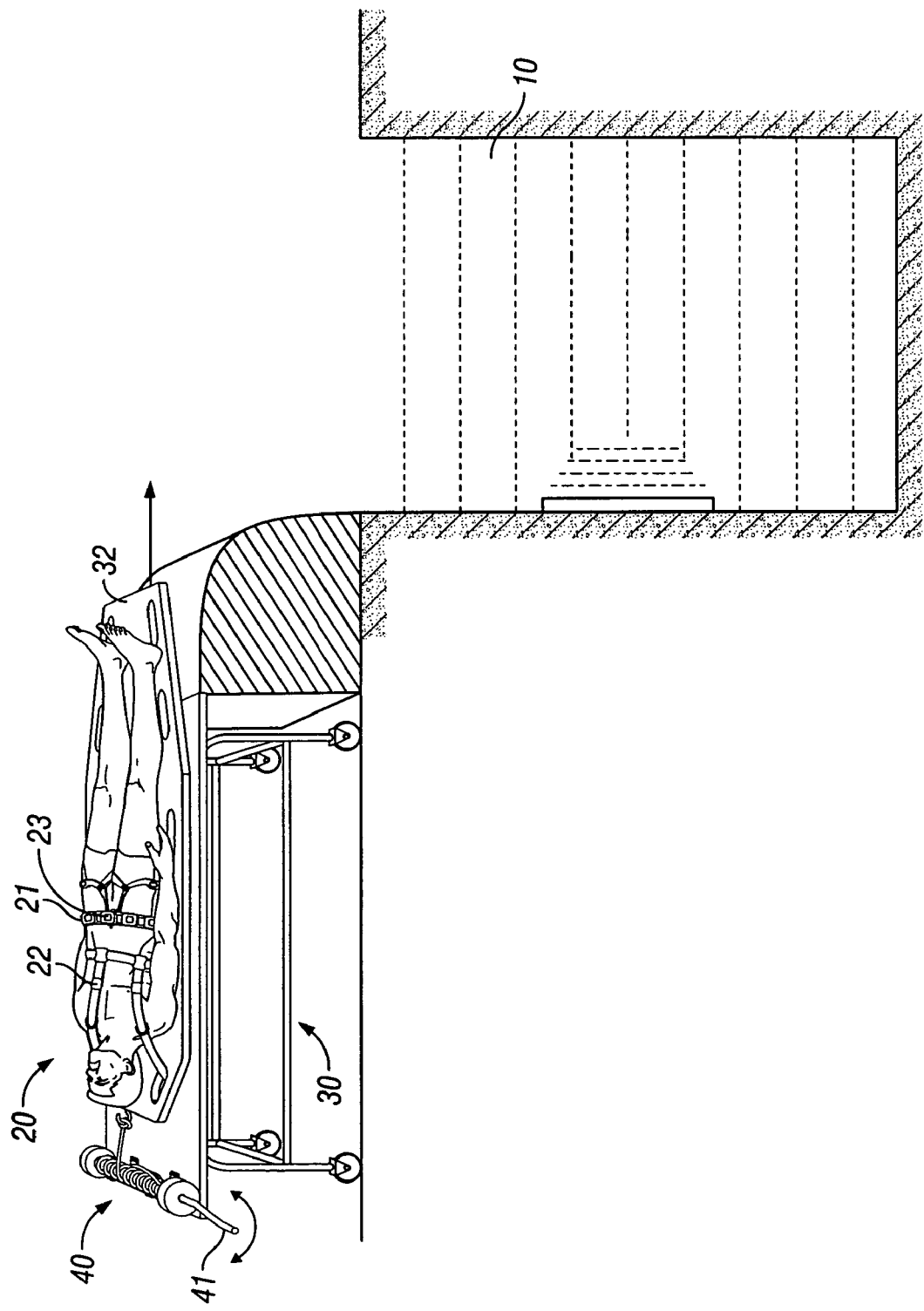

Referring to FIG. 1A, patient 20 is shown disposed on a body support board 32 which is in turn supported by stretcher 30. Stretcher 30 is wheeled adjacent the side edge of a hydrotherapy pool 10. Patient 20 is fastened to shoulder support 22 and body support board 32. This fastening secures the upper body of patient 20 for traction.

Waist harness 21 is secured to the waist and/or lower body of the patient 20. Attached to waist harness 21 are traction weights 23. Traction weight 23 is shown mounted free of body support board 32.

Figure 1B:
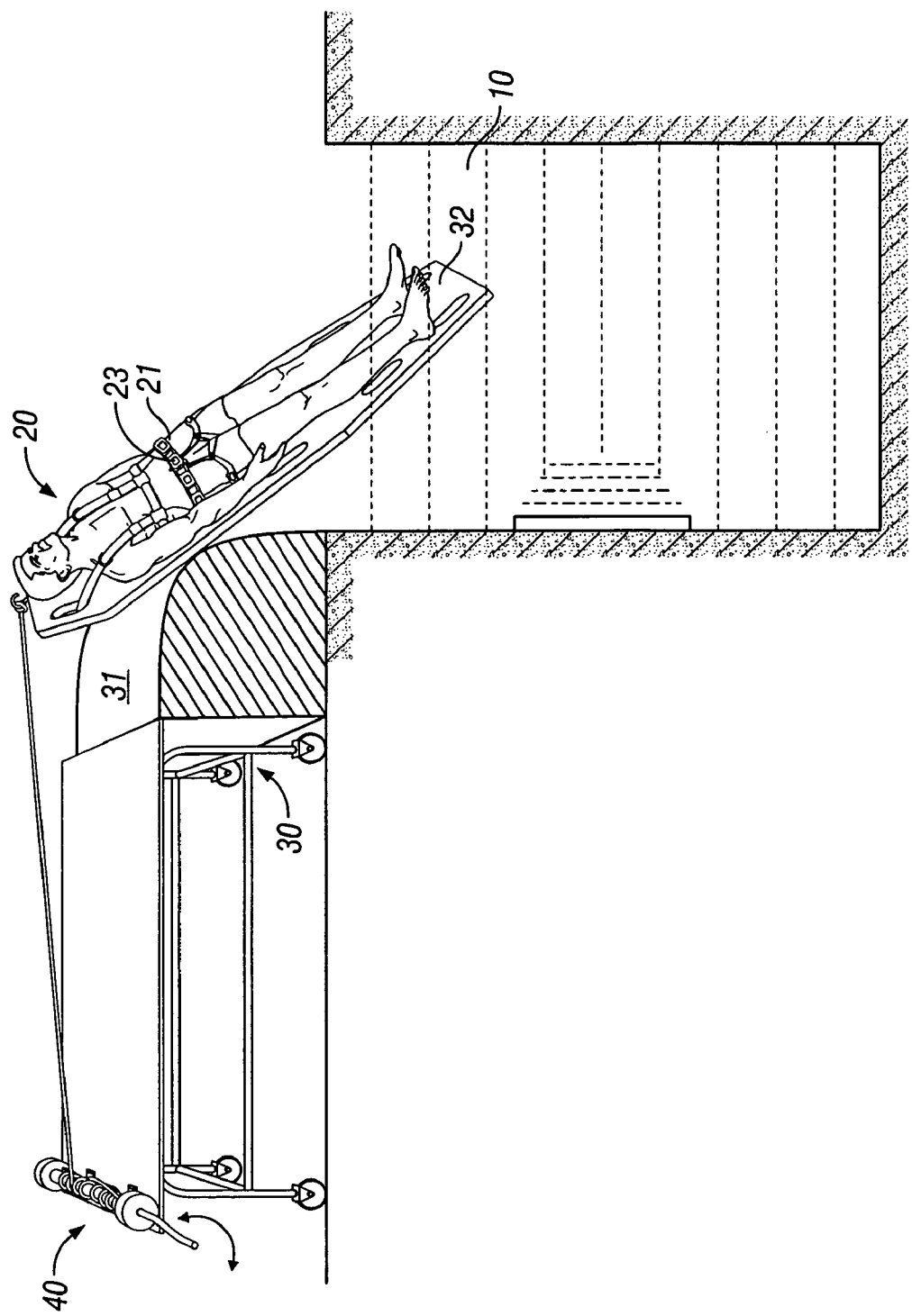

Referring to FIG. 1B, stretcher 30 is shown wheeled to the side of hydrotherapy pool 10. Stretcher 30 is shown adjacent arcuate surface 31. Arcuate surface 31 slopes from the horizontal to the vertical at the edge of the hydrotherapy pool. This enables patient 22 to first be tilted and thereafter introduced into hydrotherapy pool 10 by sliding body stretcher 32 over the arcuate surface 31. At the same time, weights 23 attached to waist harness 21 are gradually lowered with the patient into hydrotherapy pool 10 to place patient 20 in traction. Movement is schematically shown by a winch 40 with handle 42 supporting stretcher 32 at the top portion thereof. A motorized and automatic apparatus for effecting this movement is under development at the time of the filing of this Provisional Patent Application.

Figure 1C:
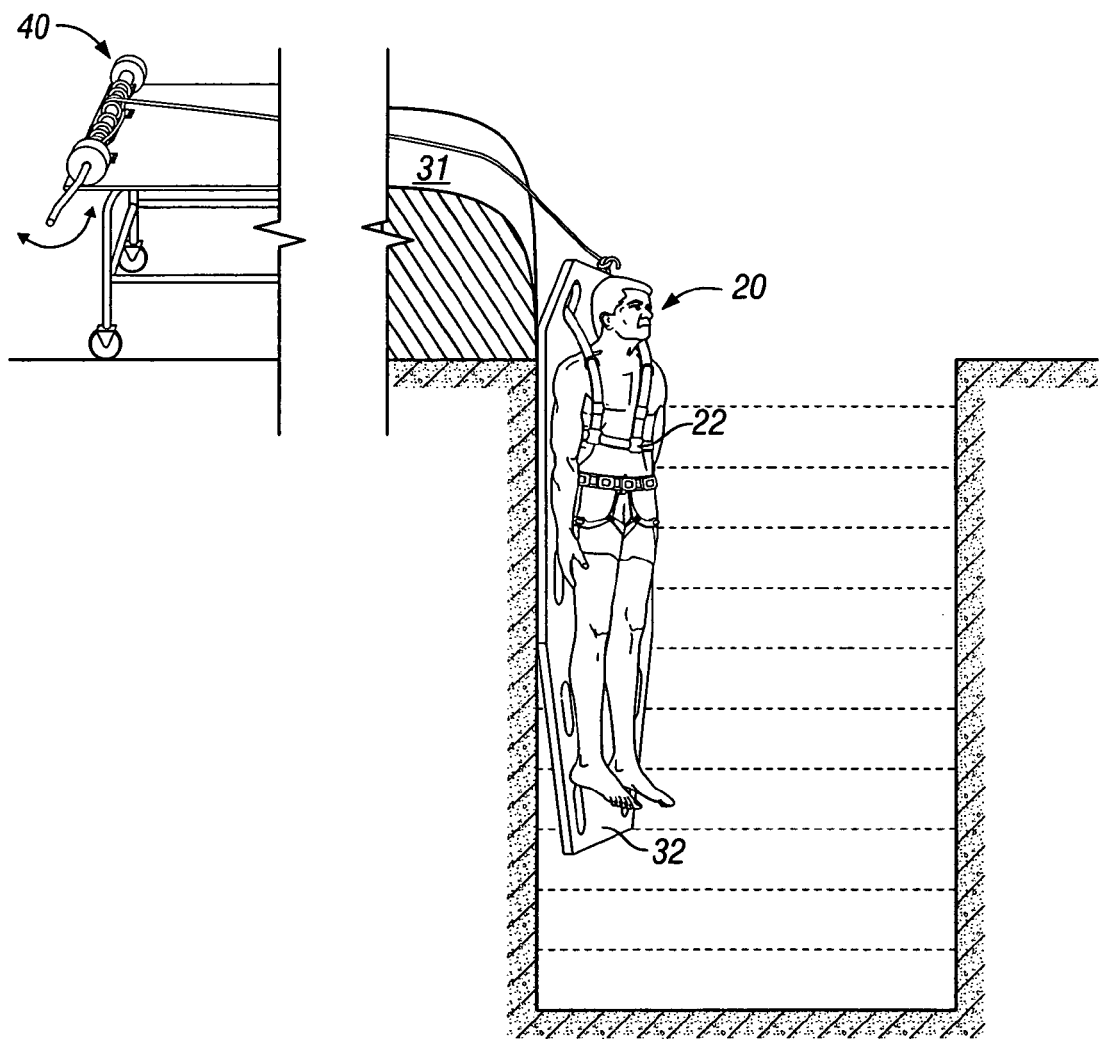

Referring to FIG. 1C, body support board 32 is shown fully in the pool. The patient can be suspended either at the side of the pool or alternatively from an independent support hook. Suspension is schematically shown by a cable from the stretcher. Preferably, patient 20 is secured to body support board 32 at shoulder support 22. At the same time, traction weights 23 pulls on the patient's lower body through waist harness 21. Traction between the shoulders of the patient and the waist of the patient is administered.

Figure 1D:
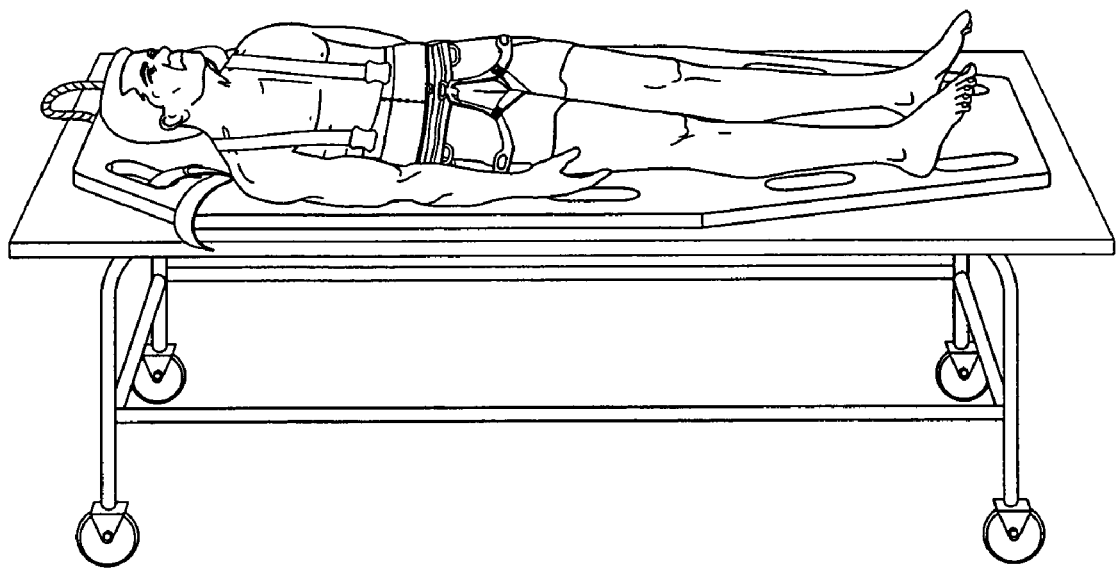

Referring to FIG. 1D, patient 20 is illustrated withdrawn from hydrotherapy pool 10 by the reverse of the process as illustrated in FIG. 1B. In this case, patient 20 has had a support belt 21 placed about his midsection at the point where traction was administered when the patient is moved to the horizontal position. When the patient is moved to the horizontal position, patient 20 is allowed to remain supine until fill relaxation from traction occurs. By maintaining patient 20 supine on body support board 32 long enough for the forces of traction to be fully relaxed, pain at the end of the hydrotherapy session is minimized.

In FIGS. 1A through 1D movement of the patient has been shown into the pool. The reader will understand that the movement from the vertical position in the pool to the horizontal position outside of the pool is the reverse of the movements of FIGS. 1A through 1C.

The reader will further understand that I preferred to support the patient at the shoulders during the hydrotherapy traction. Further, I show the weights depending from the waist of the patient.

What is claimed is:

1. A process for administering hydrotherapy traction to a patient within a hydrotherapy pool comprising the steps of:
    providing an immersible stretcher;
    providing a harness for supporting the patient from the upper body;
    providing weights for fastening about the mid- or lower body of the patient to provide traction from the upper body of the patient;
    placing the immersible stretcher in the horizontal position to receive the patient in a horizontal supine position;
    fastening the harness to support the upper body of the patient when the patient is on the stretcher in a horizontal supine position;
    fastening the weights to the mid- or lower body of the patient when the patient is on the stretcher in the horizontal supine position to provide a traction force when the patient is moved to the vertical position;
    moving the immersible stretcher from the horizontal position to the vertical position while immersing the patient in a hydrotherapy pool until the patient is in a vertical position while immersing the patient in a hydrotherapy pool until the patient is in the vertical position within the hydrotherapy pool undergoing traction between the harness and the weights along the upper body of the patient;
    leaving the patient in the vertical immersed position a sufficient period of time to administer hydrotherapy traction;
    moving the immersible stretcher from the vertical position to the horizontal position to withdraw the patient from the hydrotherapy pool and dispose the patient in the horizontal position; and
    allowing the patient to remain in the horizontal position for a sufficient period of time to gradually relax tension traction on the spine.

2. The process for administering hydrotherapy traction to a patient according to claim 1 and wherein:
    moving the immersible stretcher from the horizontal position to the vertical position while the stretcher is in the hydrotherapy pool; and,
    moving the immersible stretcher to and from the hydrotherapy pool when the stretcher is in the horizontal position.

3. The process for administering hydrotherapy traction to the patient according to claim 1 and wherein:
    the immersible stretcher is moved from the horizontal position to the vertical position to gradually remove and insert the patient to and from the hydrotherapy pool.

4. The process for administering hydrotherapy traction to a patient according to claim 1 and wherein:
    the harness and the stretcher are fastened together during moving of the patient from the horizontal position to the vertical position.

5. The process for administering hydrotherapy traction to a patient according to claim 1 and wherein:
    the provided harness fastens about the shoulders of the patient.

6. The process for administering hydrotherapy traction to the patient according to claim 1 and wherein:
    the fastening of the weights to the mid-torso of the patient includes fastening the weights to the waist of the patient.

7. Apparatus for administering hydrotherapy traction to a patient in a hydrotherapy pool comprising in combination: an immersible stretcher movable to and from a horizontal position defining an unobstructed flat surface for support of the patient; a harness for fastening to the upper body of the patient having support from above the patient, the harness having attachment to the upper body of the patient when the patient is placed-on a stretcher in a horizontal position; weights for attachment to the lower body of the patient for administering traction from the harness when the patient is moved to a vertical position, the weights having attachment to the patient when the patient is placed on the stretcher in the horizontal position; and, apparatus for disposing the immersible stretcher with the harness on the patient and the weights on the patient to and from the vertical position within the hydrotherapy pool to administer hydrotherapy traction between the harness and weights on the unobstructed flat surface of the stretcher to the patient when the patient moves to the vertical position within the hydrotherapy pool.

8. The apparatus for administering hydrotherapy traction to a patient in a hydrotherapy pool according claim 7 and further including:
    the harness for fastening to the upper body of the patient includes a harness fitted to the shoulders of the patient.

* * * * *